United States Patent
Burgio

[19]

[11] Patent Number: 6,142,780
[45] Date of Patent: Nov. 7, 2000

[54] CUSTOM TRAY FOR DELIVERING MEDICATION TO ORAL STRUCTURES

[75] Inventor: Paul A. Burgio, Grant, Minn.

[73] Assignee: 3M Innovative Properties Company, St. Paul, Minn.

[21] Appl. No.: 09/333,376

[22] Filed: Jun. 15, 1999

Related U.S. Application Data

[63] Continuation-in-part of application No. 09/240,823, Feb. 1, 1999, abandoned.

[51] Int. Cl.$^7$ .................................................. A61C 5/00
[52] U.S. Cl. .............................................. 433/80; 433/216
[58] Field of Search .............................. 433/80, 215, 216

[56] References Cited

U.S. PATENT DOCUMENTS

| | | |
|---|---|---|
| Re. 34,196 | 3/1993 | Munro ........................................ 433/215 |
| 1,934,688 | 11/1933 | Ackerman . |
| 2,257,709 | 9/1941 | Anderson . |
| 2,963,786 | 12/1960 | Browning . |
| 3,073,300 | 1/1963 | Berghash . |
| 3,247,844 | 4/1966 | Berghash . |
| 3,312,218 | 4/1967 | Jacobs . |
| 3,379,193 | 4/1968 | Monaghan . |
| 3,404,056 | 10/1968 | Baldwin . |
| 3,496,936 | 2/1970 | Gores . |
| 3,527,219 | 9/1970 | Greenberg . |
| 3,624,909 | 12/1971 | Greenberg . |
| 3,688,406 | 9/1972 | Porter et al. . |

(List continued on next page.)

FOREIGN PATENT DOCUMENTS

| | | |
|---|---|---|
| 2 002 637 | 2/1979 | United Kingdom . |
| WO 94/23610 | 10/1994 | WIPO . |
| WO 97/11676 | 4/1997 | WIPO . |
| WO 98/30381 | 7/1998 | WIPO . |
| WO 98/55044 | 12/1998 | WIPO . |
| WO 00/09036 | 2/2000 | WIPO . |

OTHER PUBLICATIONS

Pearl #2 by Joseph Blaos; Dental Economics May 1998.
Bisco, Insta–Brite, Tooth Whitening System 2 pages (no date).
Clinical Research Associates Newsletter, *Tooth Bleaching, State of Art 97*, vol. 21, Issue 4, Apr. 1997, pp. 1–3.
Home–Bleaching Technique Guide by Cary Goldstein, DDS; Dental Equipment and Supplies, Sep./Oct., 1998.
Doctor's Instructions; Nupro Gold Tooth Whitening System; Dentsply International; Rev. Jul. 1997.
Patient Instructions; Nupro Gold Tooth Whitening System; Dentsply International; Rev. Sep. 1997.
Nite White Dentist and Laboratory Instructions; Discus Dental, Inc.; undated.
Day White Dentist and Laboratory Instructions; Discus Dental, Inc.; undated.
Recommended Procedures for Fabricating a Rembrandt Bleaching Mouthguard; Denmat Corporation; 1998.
Rembrandt Lighten Bleaching Gel Instructions for Dentists; Denmat Corporation; 1996.
Opalescence Tooth Whitening Gel; Ultradent Products, Inc.; 1997.
Opalescence Dentists Instructions; Ultradent Products, Inc.; 1997.

*Primary Examiner*—Ralph A. Lewis
*Attorney, Agent, or Firm*—James D. Christoff

[57] ABSTRACT

A dental tray for delivery medication to oral structure is custom-made to closely match the configuration of the oral structure. A lingual wall of the tray includes a lingual edge section having an outer edge that is spaced in a gingival direction from the patient's gingival margin a certain distance in order to reduce the possibility of adverse effects as might be caused by movement of the patient's tongue. A buccolabial wall of the tray has an outer edge that is closely adjacent the patient's gingival margin in order to increase patient comfort, reduce gingival irritation and improve patient compliance during the course of treatment.

17 Claims, 2 Drawing Sheets

U.S. PATENT DOCUMENTS

| | | | |
|---|---|---|---|
| 4,044,762 | 8/1977 | Jacobs . | |
| 4,063,552 | 12/1977 | Going et al. . | |
| 4,064,628 | 12/1977 | Weitzman . | |
| 4,138,814 | 2/1979 | Weitzman . | |
| 4,267,167 | 5/1981 | Weitzman et al. | 424/52 |
| 4,290,174 | 9/1981 | Kalleberg . | |
| 4,368,040 | 1/1983 | Weissman | 433/36 |
| 4,401,616 | 8/1983 | Wagner | 264/138 |
| 4,560,351 | 12/1985 | Osborne | 433/80 |
| 4,569,342 | 2/1986 | von Nostitz . | |
| 4,657,508 | 4/1987 | Dellinger . | |
| 4,776,792 | 10/1988 | Wagner et al. | 433/71 |
| 4,984,339 | 1/1991 | Provost et al. . | |
| 5,076,791 | 12/1991 | Madray, Jr. | 433/215 |
| 5,085,585 | 2/1992 | Zimble . | |
| 5,098,303 | 3/1992 | Fischer | 433/215 |
| 5,152,917 | 10/1992 | Pieper et al. . | |
| 5,165,424 | 11/1992 | Silverman . | |
| 5,234,342 | 8/1993 | Fischer | 433/215 |
| 5,240,415 | 8/1993 | Haynie | 433/216 |
| 5,330,357 | 7/1994 | Keller | 433/215 |
| 5,376,006 | 12/1994 | Fischer | 433/215 |
| 5,409,631 | 4/1995 | Fischer | 252/186 |
| 5,460,527 | 10/1995 | Kittelsen | 433/215 |
| 5,500,273 | 3/1996 | Holmes et al. | 428/147 |
| 5,536,168 | 7/1996 | Bourke . | |
| 5,562,449 | 10/1996 | Jacobs et al. | 433/215 |
| 5,573,399 | 11/1996 | McClintock, II | 433/80 |
| 5,575,654 | 11/1996 | Fontenot | 433/80 |
| 5,575,655 | 11/1996 | Darnell | 433/216 |
| 5,702,251 | 12/1997 | McClintock, II | 433/80 |
| 5,707,235 | 1/1998 | Knutson | 433/213 |
| 5,725,843 | 3/1998 | Fischer | 424/49 |
| 5,746,598 | 5/1998 | Fischer | 433/216 |
| 5,759,037 | 6/1998 | Fischer | 433/215 |
| 5,759,038 | 6/1998 | Fischer | 433/215 |
| 5,770,105 | 6/1998 | Fischer | 252/186.25 |
| 5,816,802 | 10/1998 | Montgomery | 433/80 |
| 5,842,860 | 12/1998 | Funt . | |
| 5,863,202 | 1/1999 | Fontenot et al. . | |

CUSTOM TRAY FOR DELIVERING MEDICATION TO ORAL STRUCTURES

This application is a continuation-in-part of Ser. No. 09/240,823 filed on Feb. 1, 1999, now abandoned.

BACKGROUND OF THE INVENTION

1. Field of the Invention

The present invention relates to a tray for delivering medication to the teeth and/or gingiva of a dental patient. More particularly, the field of the present invention concerns a dental medication delivery tray that is custom-made to closely match the configuration of at least part of a patient's dental arch.

2. Description of the Related Art

A variety of methods have been proposed in the past to deliver medication to the teeth and/or gingiva (i.e., the gum tissue) of a dental patient. One method of applying medication to teeth involves direct application of the medication to the tooth surface by the use of a brush, swab or the like. This method is relatively inexpensive and can be carried out either by the dental practitioner or by the patient.

Unfortunately, the direct application of a medicant to oral structures is generally unsatisfactory because the medication typically does not remain on the oral structure for a significant length of time. The length of time is variable and may depend on factors such as the viscosity of the medication, the presence of saliva and the ability of the patient to prevent adjacent soft tissues such as inner surfaces of the labia or lips and bucca or cheeks from contacting the tray containing the medication. In many instances, the effectiveness of the medication is substantially diminished if the medication is prematurely removed from the oral structure under treatment.

Another common method for delivering medication to teeth involves the use of a dental tray that is placed over the dental arch. The tray has a channel that receives the teeth and has a length that is sufficient to receive all or at least a portion of the dental arch. In some instances, the channel has a sufficient depth to receive a portion of the gingiva along with the teeth.

Many dental medication delivery trays are mass-produced and not custom made to closely fit the dental arch of a particular patient. Although such trays are relatively inexpensive, they are often considered quite bulky and unpleasant to wear for any significant length of time. Additionally, some mass-produced dental trays do not retain medication against the oral structures under treatment unless the patient remains relatively immobile.

Dental trays that are custom-made to closely fit the dental arch of a patient are considered by many to represent a significant improvement over mass-produced dental trays. The close fit provided by custom-made trays largely avoids unnecessary void spaces that are common with mass-produced dental trays. Most custom-made trays are less obtrusive in the mouth than mass-produced trays, and as such are more comfortable to wear for extended periods of time.

One technique of making a custom dental tray involves taking an alginate impression of a patient's dental structure, and then making a model or casting from the impression. Next, a thin sheet of heat softenable plastic material is placed over the casting and heated, causing the plastic sheet to drape over the model and ultimately form a configuration that closely matches the shape of the underlying model. The tray is then trimmed as needed.

One of the most common uses of both mass-produced and custom-made dental medication trays is in connection with a bleaching gel or solution to whiten the patient's teeth. Many individuals desire whiter teeth and seek to eliminate or at least reduce the discoloration of stained teeth. Tooth stains are caused by a variety of sources, including food and beverages, drugs (such as tetracycline), tobacco products and poor oral hygiene.

When dental trays are used for bleaching teeth at home, the patient is typically instructed to place an amount of bleaching solution into a corresponding area of the tray for each tooth to be treated. The tray is then placed over the dental arch. Often, the bleaching solution is changed every 0.5 to 2.5 hours and the tray is removed during meals. Sometimes a recommendation is made to wear the dental tray overnight. The efficacy of the bleaching procedure depends on factors such as the type and intensity of the stain, the bleaching agent contact time on the tooth surfaces, the amount of available active ingredient in the bleaching solution as well as patient acceptance and adherence to the procedure.

Unfortunately, the volume of bleaching solution that is available in conventional trays tends to diminish rapidly over time, thereby decreasing the amount of active ingredient available for bleaching the teeth. Test results in the April, 1997 issue of the *Clinical Research Associates Newsletter* show that in many instances after 30 minutes, less than 50% of the original quantity of bleaching agent was available for bleaching activity. The same test results show that in many instances after one hour, less than 25% of the bleaching agent was available for bleaching activity. Consequently, it is often recommended to replenish the bleaching agents in conventional trays about every 15 to 30 minutes in order to maintain the most efficacious dosage of bleaching agent in contact with the tooth.

Unfortunately, the daytime schedules of many patients do not easily accommodate periodic, continuous replenishment of the bleaching agent. In addition, periodically replenishing the bleaching agent during the night is unrealistic for many patients. Since patient adherence to the procedure determines the ultimate success of the treatment program, the need to constantly replenish the dental bleaching solution is a major obstruction that limits the success of the treatment.

SUMMARY OF THE INVENTION

The present invention is directed in one aspect to a custom-made medication delivery tray for delivering medication to tooth structure of a dental patient. The tray comprises a body having a base, a buccolabial wall and a lingual wall. The base, the buccolabial wall and the lingual wall present a channel that is generally complemental in configuration to the patient's tooth structure. The buccolabial wall extends at least in part along the gingival margin of the buccolabial side of the tooth structure without contacting the gingiva. The lingual wall extends along a line that is spaced at least in part at least 4 mm. in a gingival direction from the gingival margin of the tooth structure on a lingual side of the tooth structure.

Another aspect of the present invention relates to a method of making a medication delivery tray for delivering medication to the dental structure of a patient. The method comprises the acts of providing a model of at least a portion of a dental arch, and forming a sheet member over at least part of the model. The method also includes the act of trimming the sheet member to make the tray. The act of trimming the sheet member includes the act of trimming the sheet member along a path corresponding to a line spaced no greater than 2.0 mm in an occlusal direction from the gingival margin of the model on a buccolabial side of the model. The act of trimming the sheet member also includes the act of trimming the sheet member along a path corresponding to a line that is spaced at least in part at least 4 mm. in a gingival direction from the gingival margin of the model on a lingual side of the model.

The present invention has been found to significantly enhance retention of medication such as bleaching solution in the tray in comparison to conventional trays. The section of the lingual wall of the tray that extends past the gingival margin provides an effective seal that resists movement of the medication in a direction from a lingual side to a buccolabial side of the arch and ultimately out over the gingival edge of the tray along the buccolabial wall. Moreover, by extending the lingual wall at least 4 mm. past the gingival margin, a comfortable area is presented to receive the patient's tongue and it is less likely that the tongue will engage the edge of the lingual wall and urge the tray away from the arch. The lingual extension also provides better stability of the tray in use so that the tray does not substantially rock or shift relative to the underlying arch.

These and other aspects of the invention are set out more fully in the detailed description that follows and are illustrated in the accompanying drawings.

DETAILED DESCRIPTION OF THE PREFERRED EMBODIMENTS

Figure 1:
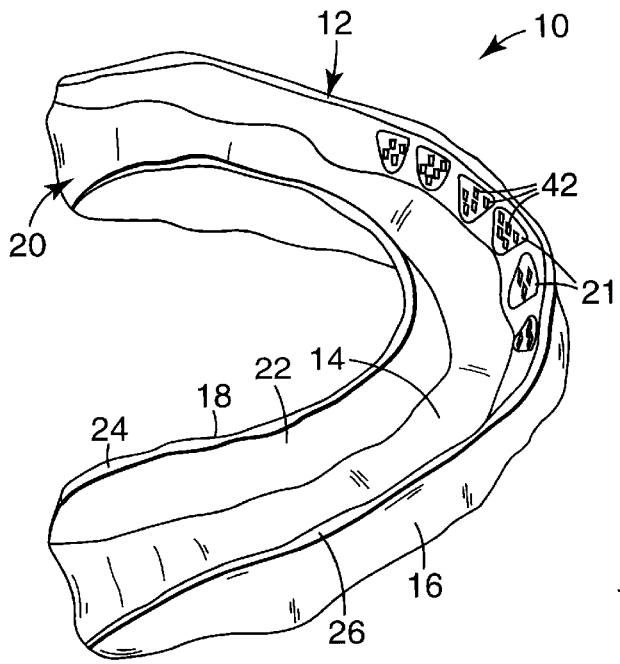
FIG. 1 is a perspective view of an exemplary medication delivery tray constructed in accordance with certain embodiments of the present invention.

A custom-made medication delivery tray for delivering medication to tooth structure of a dental patient according to one embodiment of the invention is illustrated in FIG. 1 and is broadly designated by the numeral 10. The tray includes a body 12 having a base 14, a buccolabial wall 16 (i.e., a wall next to the patient's lips or cheeks) and a lingual wall 18 (i.e., a wall next to the patient's tongue). The base 14 and the walls 16, 18 combine to present an elongated channel 20.

The channel 20 has an overall, generally "U"-shaped configuration in reference planes perpendicular to the longitudinal axis of the channel 20. Moreover, the body 12 as well as the channel 20 have an overall, generally "U"-shaped configuration in plan view or when considered in a reference plane containing the longitudinal axis of the channel 20. Preferably, the body 12 extends a distance equivalent to the entire length of the patient's arch or at least a substantial majority of the length of the patient's dental arch, although other constructions are also possible. For example, the tray 10 and the channel 20 may extend along only the patient's anterior teeth, or only along one quadrant of one dental arch.

Preferably, the channel 20 is generally complemental in configuration to the patient's dental arch so that unnecessary void spaces between the tray and the patient's oral structures are avoided and the resulting tray is not considered obtrusive when worn in the mouth. As an option, however, small recesses or wells 21 may be made along the inner surface of the buccolabial wall 16 adjacent the facial surface of each tooth in order to provide a pocket for receiving a quantity of the medication. Optionally, the wells 21 are provided only along the patient's anterior, cuspid and bicuspid teeth as may be useful, for example, when the tray 10 is used for delivering a bleaching composition to the most visible teeth. However, if the patient's molar teeth are also heavily stained, it may be desirable to provide such wells in areas of the buccolabial wall 16 adjacent such molar teeth as well.

The lingual wall 18 includes a peripheral edge section 22. The edge section 22 has an outer edge 24 that extends along a line that is spaced at least in part and preferably spaced along substantially its entire length at least 4 mm. in a gingival direction from the gingival margin of the lingual side of the patient's dental arch receiving the tray 10. More preferably, the outer edge 24 extends along a line that is spaced at least in part (and more preferably is spaced substantially along its entire length) a distance of 6 mm. in a gingival direction from the gingival margin of the patient's dental arch along its lingual side. Optionally, the edge 24 is spaced no greater than 20 mm. and more preferably less than 12 mm. in a gingival direction at any point from the gingival margin of the lingual side of the dental arch.

The preferred spacing of the edge 24 from the gingival margin along the lingual side of the dental arch as mentioned in the previous paragraph is provided at least in regions adjacent the patient's anterior teeth (i.e., in regions adjacent the patient's central and lateral incisors). Optionally, the edge 24 approaches the gingival margin and the edge section 22 narrows in width as either end of the channel 20 is approached. For example, the edge 24 may be as close as 2 mm., or optionally directly adjacent the patient's gingival margin in regions next to the patient's molar teeth.

As another option, the tray 10 when made to fit the upper arch includes palatal section that extends across a majority of the patient's palate and is integrally connected to the lingual wall 18. In that instance the outer edge is spaced a distance greater than 12 mm. from the gingival margin at least in regions next to the anterior teeth.

The buccolabial wall 16 has an outer edge 26 that extends along the gingival margin of the patient's dental arch on a buccolabial side of the teeth. Preferably, the outer edge 26 is located up to 2.0 mm, and more preferably only up to 1.0 mm, in an occlusal direction from the gingival margin and does not contact the gingival margin of the patient's dental arch when the tray is in use in the oral cavity. Preferably, the edge 26 has a scalloped configuration that precisely matches the contoured shape of the adjacent gingival margin. Alternatively, however, the edge 26 could extend along the gingival margin in a generally straight path and pass across the location of each tooth where the gingival margin reaches an apex in a gingival direction (i.e., the location of each tooth, typically near the center of each tooth, where the exposed enamel extends the greatest distance in a gingival direction; in this alternative, the buccolabial wall 16 completely covers each gingival papilla that extends in an occlusal direction toward an interproximal region between adjacent teeth. The location of the outer edge 26 as described above helps ensure that the tray 10 does not irritate the soft gingival tissue of the buccolabial side of the arch. Gingival irritation from abrasion from the tray in this region when combined with the presence of certain medications (such as bleaching compositions) might otherwise result in the formation of highly unpleasant sores.

A custom or custom-made dental tray refers to a dental tray that is made using a mold, casting or other model of the patient's dental structures. Custom dental tray also refers to a dental tray that is made using digital data representative of the patient's dental structure as described in further detail below. Dental structures and oral structures refer to the teeth and/or gingiva.

Figure 2:
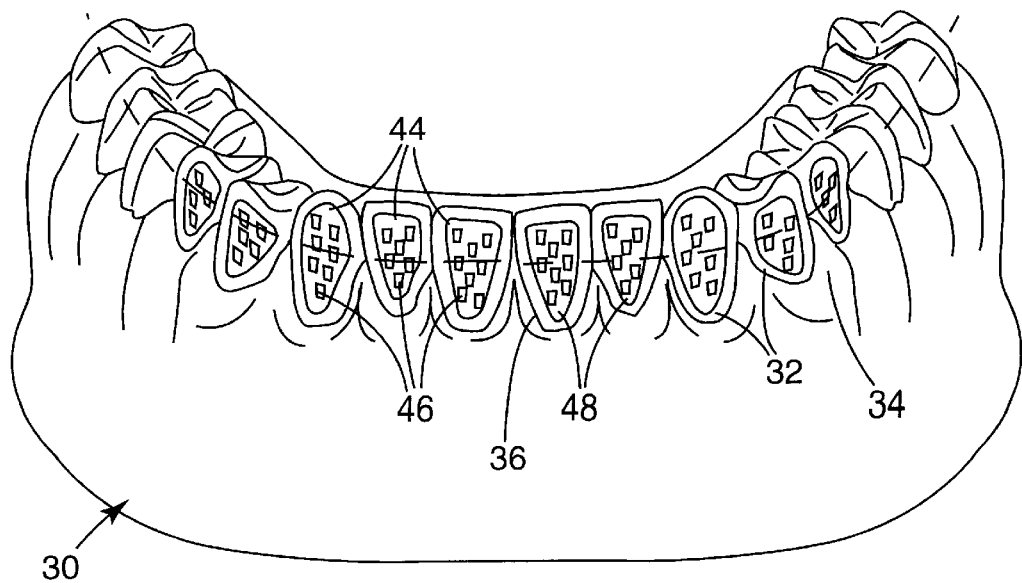
FIG. 2 is a perspective view of an exemplary model of a patient's dental arch as may be useful in making the tray shown in FIG. 1.

FIG. 2 is a perspective view of an example of a casting or model 30 that is a replica of one dental arch of the patient's dental structure. One method of making the model 30 involves first taking an impression of the patient's dental structure using an alginate impression material or other suitable impression material. The model 30 may be a replica of either the patient's upper or lower dental arch.

In the example of the model 30 as shown in FIG. 2, the model 30 includes a number of model teeth 32 representing the teeth of the patient's selected dental arch. In addition, the model 30 includes model gingival tissue 34 that is a replica of the patient's gingival tissue of the selected dental arch. In FIG. 2, a model gingival margin is designated by the numeral 36 and generally has the appearance of a scalloped line extending along the model arch and along a path that follows the line of differentiation between the replica enamel of each model tooth 32 and the adjacent model gingival tissue 34.

A preferred method of making the tray 10 includes providing a sheet member that is made of a thermoplastic material such as polypropylene, ethylene or vinyl acetate, such as ethylene vinyl acetate (EVA). Suitable EVA materials include, for example, 0.04 in. (1.0 mm.) thick EVA vacuum forming material (Catalog No. 089-5003, from Patterson Dental Supply, Inc.). EVA is commercially available and approved for oral use by the U.S. Food and Drug Administration. These materials are easily thermoformed or vacuumed formed over the model 30 using conventional techniques. Preferably, the sheet member has a thickness no greater than 0.080 in (2.0 mm) and is translucent.

Figure 3:
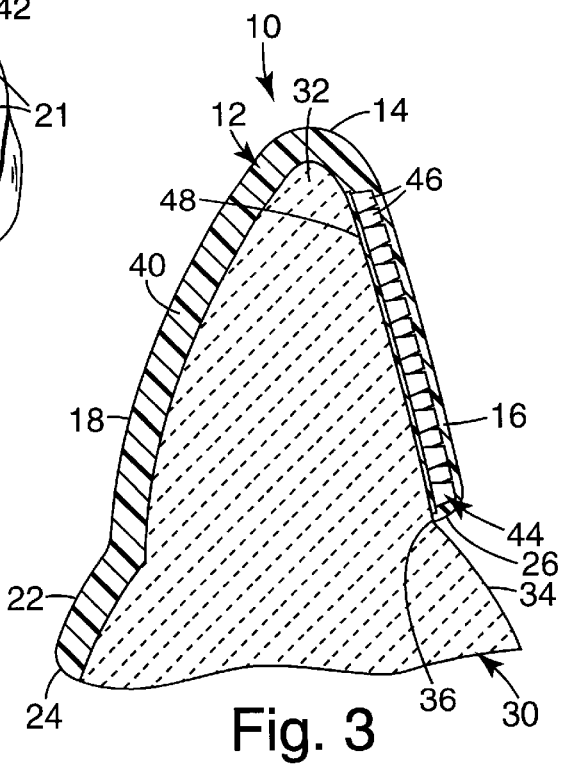
FIG. 3 is an enlarged side sectional view of the model illustrated in FIG. 2 along with a sheet of plastic material that has been formed over the model to make the tray of FIG. 1.

Once the sheet member has been formed over the model 30, the sheet member is trimmed according to the principles of the present invention. FIG. 3 is a sectional illustration of an exemplary sheet member 40 that has been formed over one of the model teeth 32 and a portion of the model gingival tissue 34. As shown, the sheet member 40 has assumed a configuration closely complemental to underlying areas of the model tooth 32 and the model gingival tissue 34.

The sheet member 40 is trimmed so that the resulting tray 10 has a buccolabial wall 16 and lingual wall 18 as described above. The sheet member 40 may be trimmed with a scissors, a knife or any other suitable tool as desired. Optionally, a pencil or ink marking may be made on the sheet member 40 while the tray 10 is on the model 30 to serve as a guide for trimming once the tray 10 has been removed from the model 30. As another option, a knife is used to trim the tray 10 while the tray 10 is still in place on the model 30. The placement of such guide lines is facilitated when the sheet member 40 is made of a transparent or translucent material having sufficient light transmittance to allow the practitioner to see the model gingival margin through the sheet member 40 while the sheet 10 is received on the model 30.

It has been found that the lingual edge section 22 is a significant advantage, in that the edge section 22 provides an effective seal that helps to reduce the flow of saliva into the channel 20. When the tray 10 is in use, the patient's tongue may bear against the lingual wall 18, and in some instances may bear against the lingual wall 18 at repeated, spaced apart intervals of time. Such pressure on the lingual wall 18 tends to establish a "pumping" action that causes movement of water, saliva and/or medication.

The pumping action caused by the tongue creates a hydrodynamic force that tends to move the water, saliva and/or medication in the tray 10 in various directions. One direction of movement is in a direction from the lingual wall 18 to the buccolabial wall 16 over the occlusal tips of the teeth, and toward the gingival edge of the buccolabial wall 16. The lingual edge section 22 provides a flap of material that functions as a seal to resist and hinder such flow.

Additionally, many patients have a tendency to fidget with dental trays when the tray is in use. For example, many patients, whether consciously or unconsciously, use their tongue to "play" with the gingival edge of the tray along its lingual side. Disturbing of the outer edge in such fashion is a disadvantage, in that the tongue may unintentionally lift the outer edge on the lingual side and enable the medication to escape. Lifting of the gingival edge may also enable additional saliva or water to enter the tray channel, thus diluting the medication in the tray and/or enhancing the hydrodynamic "pumping" action the next time that the tongue is pressed against the lingual wall of the tray.

The lingual edge 24 of the present invention is a significant advantage in that it is spaced a significant distance from the gingival margin of the lingual side of the patient's dental arch. That spacing hinders the patient's tongue from lifting the lingual edge section 22 and many of the problems described above are consequently avoided. As a result, medication in the channel 20 remains in place for a greater length of time than would otherwise be possible and more effectively treats the dental structure of interest.

The present invention is also beneficial because the tray 10 can be made from a relatively thin sheet member, resulting in a tray that is less obtrusive in the mouth. In the past, dental trays were often made of a material having a thickness ranging from about 0.08 in. (2 mm.) to about 0.15 in. (3.8 mm.) since such materials tend to be better at resisting hydrodynamic forces than dental trays made from thinner materials. However, because the lingual edge section 22 of the present invention provides an effective seal that reduces the flow of medication, saliva and/or water the channel 20, the tray 10 can be made from a relatively thin sheet member (such as 0.04 in., or 1 mm. as described above). Moreover, use of a relatively thin sheet member increases the flexibility of the lingual edge section 22 so that the edge section 22 readily shifts as needed to closely contact the underlying tissue and quickly establish a good seal against adjacent soft tissue.

Optionally, each of the wells 21 that is located along the buccolabial wall 16 of the tray 10 contain a plurality of support members 42 (shown in FIG. 1 but not to scale) that extend in a lingual direction to engage the patient's dental structure. These support members 42 are preferably discreet and free standing and resist compression of the reservoirs as might otherwise occur due to hydrodynamic forces and/or movement of the tray 10 in the patient's oral cavity.

One method of making the support members 42 involves the use of appliques 44 such as are shown in FIG. 2. In this method, an applique 44 is applied to buccolabial surfaces of the model teeth 32. The overall shape of the applique 44 is selected to match to the desired, overall shape of the corresponding well 21. A suitable adhesive is used to affix the appliques 44 to the selected model teeth 32.

Each applique 44 includes a series of protrusions 46 that project outward from a backing 48 as illustrated in FIG. 3. In this embodiment, the protrusions 46 serve as a mold for molding the support members 42 in the sheet member 40. The appliques preferably remain on the model 30 as the molded tray 10 is detached from the model 30 so that further handling of individual appliques 44 is avoided. Once the tray 10 is detached from the model 30 and the appliques 44, the wells 21 with the support members 42 are exposed and present a configuration that represents the inverse of the shape of the appliques 44.

The protrusions 46 and/or the resulting support members 42 can have a variety of geometric shapes in cross section, such as rectangular, circular, semi-circular, triangular, square, hexagonal, and the like. The support members 42 may assume a variety of shapes, such as cones, truncated cones, rods, pyramids, truncated pyramids, cubes, gum drops, cylinders, nail heads or mushroom-shaped members, and the like. The outer ends of the support members 42 may be flat, rounded, pointed or a variety of other shapes, as determined by the shape of the spaces between the protrusions 46 and the optional land areas between the protrusions 46. The appliques 44 may have a micro-replicated surface that is accomplished by using a variety of methods, such as disclosed in U.S. Pat. Nos. 5,152,917 (Pieper, et al.) and 5,500,273 (Holmes et al.).

The protrusions 46 may be discrete and spaced apart from each other. Alternatively, the protrusions 46 may be integrally interconnected to form one or more networks of protruding structure. For example, the protrusions 46 may present an ordered or random configuration. An example of an ordered configuration includes a honeycomb pattern where optionally one or more honeycombs may be separated or decoupled from adjacent honeycombs. Other examples of an ordered configuration include oral structures and elongated rails.

Optionally, if the projections 46 are the support members 42, the projections 46 (such as, for example, the oval or honeycomb structures) may have a small medication-receiving recess or cavity at their outer ends that presents the oval or honeycomb (i.e., hexagonal) appearance. Preferably, the protrusions 46 have sufficient stiffness or rigidity so that the recess or cavity does not collapse under the forces present in the oral cavity during use. In this manner, the medication tends to remain in the cavities for a longer period of time.

As an alternative, the appliques 44 may be embedded and integrally molded with the sheet member 40 during molding of the sheet member 40. In this alternative, appliques 44 are reversed from their orientation shown in FIG. 3 so that the protrusions 46 serve as the support members 42. Optionally, a section of double-sided adhesive tape extends across outer ends of the protrusions 46 in this embodiment to temporarily retain the appliques 44 on the model 30 during molding of the sheet member 40.

Figure 4:
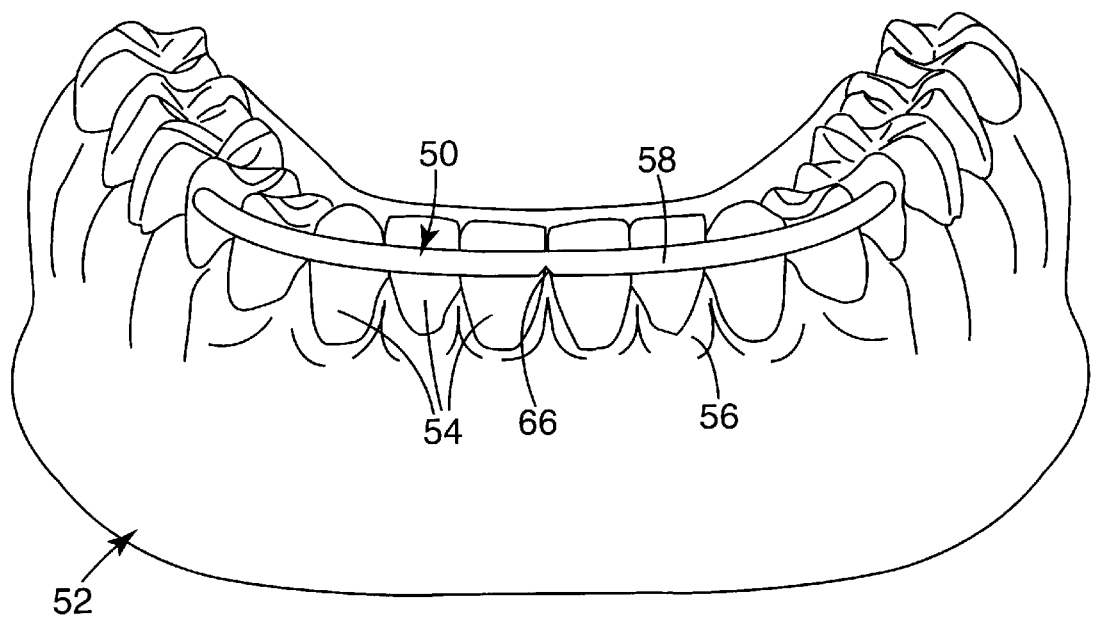
FIG. 4 is a perspective view of an exemplary model of a patient's dental structure along with an applique for making a medication delivery tray according to alternative embodiments of the invention.

FIG. 4 is an illustration of an applique 50 that is provided on a model 52 according to other embodiments of the invention. The model 52 is identical to the model 30, and includes a series of model teeth 54 as well as gingival tissue 56.

The applique 50 has an elongated strip configuration to engage with portions of the model 52 corresponding to portions of multiple teeth. In the embodiment shown in FIG. 4, the applique 50 extends from one second bicuspid tooth to the other. However, if the patient's molar teeth are heavily stained, it may be desirable to provide a somewhat longer applique in order to extend over the molar tooth surfaces as well.

Figure 5:
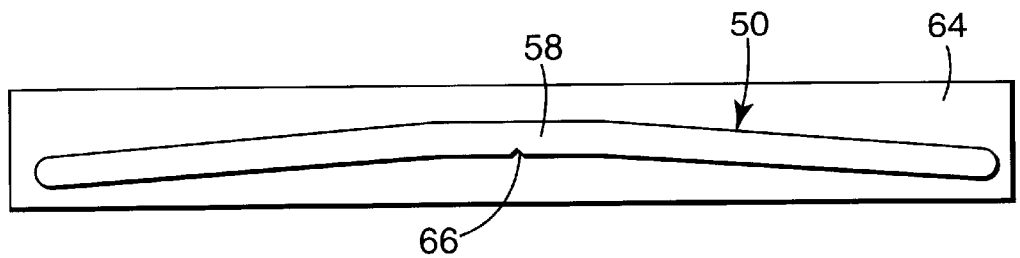
FIG. 5 is a side elevational view of the applique alone that is shown in FIG. 4 as it appears before placement on the model, wherein the applique is carried on a release liner.
Figure 6:
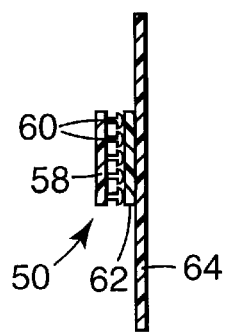
FIG. 6 is an end cross-sectional view (not to scale) of the applique and release liner shown in FIG. 5.

As shown in more detail in FIGS. 5 and 6, the applique 50 includes a backing layer 58 and a number of protrusions 60 connected to the backing layer 58. The protrusions 60 provide the discreet, freestanding support members described above. Preferably, the protrusions 60 (as well as the support members 42 in FIG. 1) are arranged to define tortuous paths. A tortuous path refers to a passageway or conduit that is not substantially straight and extends past the sides of a plurality of protrusions 60 (or support members) in the spaces between adjacent protrusions 60 (or support members). The tortuous paths are preferably arranged to increase flow resistance in a gingival direction through the resulting reservoir and/or in a mesial-distal direction along the length of the tray channel. To the extent that any segment of the tortuous paths is straight, that segment is preferably skewed with respect to the gingival direction or the mesial-distal direction of the channel. Optionally, the protrusions or support members are constructed of a hydrophilic material.

In general, the number of protrusions 60 (or support members 42) per unit area is preferably in the range of about 78 per square cm. (500 per sq. in.) to about 465 per sq. cm. (3000 per sq. in.). An example of a suitable number is about 144 per sq. cm. (900 per sq. in.). However, a higher or lower number of protrusions 60 or support members 42 per unit area may be optimal in certain circumstances and the optimal number may depend on factors such as the nature of the sheet member material forming the tray, the characteristics of the medication and the height, shape and diameter of the protrusions 60. The height of the protrusions 60 or support members 42 is preferably in the range of about 0.5 mm. to about 1.5 mm., although longer or shorter protrusions 60 or support members 42 may be used for specific applications, depending upon the viscosity of the medication, the nature of the treatment, the specific dental structure being treated, etc.

The protrusions 60 that are illustrated in FIG. 6 each include a stem that projects outwardly from the backing layer 58 as well as an enlarged head. Various manufacturing processes for forming an array of upstanding headed stems integral with a backing layer are described in U.S. Pat. No. 4,290,174 (Kalleberg) U.S. Pat. No. 4,984,339 (Provost et al.), WO 94/23610 (Miller et al.), WO 98/30381 (Miller et al.) and PCT/US97/15960 (Kempfer).

Optionally, the protrusions 60 are made by a micro-replication process. An example of a suitable applique is a die-cut section of the hook side of a polypropylene micro-replicated mechanical fastener such as no. CS-200 diaper tape from 3M Company. Optionally, the protrusions 60 may be identical or similar to the protrusions 46 mentioned above.

An adhesive tape 62 is releasably connected to the enlarged heads of the protrusions 60. An example of a suitable adhesive tape is a medical grade double-sided adhesive tape such as no. 1522 from 3M Company. As an alternative, a layer of adhesive may be provided in place of the adhesive tape 62.

The adhesive tape 62 is also initially connected to a release liner 64 to facilitate handling of the applique 50 before the applique 50 is applied to the model 52. Suitable materials for the release liner 64 include a section of poly(ethylene terephthalate) ("PET") sheeting that is coated with silicone to enhance release of the adhesive.

In use, the applique 50 and the adhesive tape 62 are detached from the release liner 64 and trimmed as necessary. The applique 50 and the adhesive tape 62 may be trimmed after being initially placed on the model 50 or alternatively trimmed before detachment from the release liner 64. The applique 50 is trimmed to a length sufficient to extend across all of the tooth surfaces intended to receive medication.

Preferably, a gingival edge of the applique 50 includes a notch 66 that is located in the center of the applique 50 along its length. When the applique 50 is placed on the model 52, the practitioner places the notch 66 along the midline (i.e., in the center of the dental arch of the model 52), so that the applique 50 is properly centered on the model 52. The notch 66 provides a visual alignment guide to facilitate placement of the applique 50 on the model 50. Preferably, the applique 50 is aligned to the mid-third of the model teeth 54 in an occlusal-gingival direction as shown in FIG. 4.

Preferably, but not necessarily, the applique 50 is initially curved in a wide arc when attached to the release liner 64 as can be observed by reference to FIG. 5. The arc-shaped configuration of the applique 50 facilitates conforming the applique 50 to the buccolabial tooth surfaces of the model 52 as the applique 50 is attached to the model 52. Optionally, the practitioner may apply finger pressure to the applique 50 in areas extending over interproximal regions of the dental arch in order to better conform the applique 50 to the curvature of the individual model teeth 54.

Next, a dental medication delivery tray is formed over the model 52 and the applique 50. For example, a sheet member of thermoplastic material may be thermoformed or vacuum formed over the model 52 and the applique 50. Suitable thermoplastic materials include, for example, the EVA materials described above. Preferably, the applique 50 both chemically and mechanically bonds to the thermoplastic material in order to remain non-removably affixed in place in the tray.

The resultant dental tray is then removed from the model 52. Preferably, the adhesive tape 62 preferentially adheres to the model 52, so that as the tray is pulled from the model 50 the adhesive tape 62 detaches from the applique 50 and remains on the model 52. The tray is trimmed as described above in connection with the tray 10. In use, medication such as a dental bleaching agent is applied to the applique 50 in the tray and the tray is then placed over the patient's dental arch.

Use of the applique 50 is a significant advantage over conventional tray fabrication techniques, in that the applique 50 can be applied to a plurality of model teeth 54 at once and preferably to all of the model teeth 54 that correspond to the patient's teeth to be treated. As a result, application of a reservoir-making material to the surface of each model tooth 54 on an individual basis can be avoided and the total time required to make the tray is substantially reduced. The tray is preferably made with the applique 50 permanently bonded to the thermoplastic material, although as an alternative the applique 50 may be placed over the model teeth 54 with its protrusions 60 facing outwardly (i.e. buccolabially) such that an impression of the applique 50 is formed in the thermoplastic material to create the reservoir and support structures.

As illustrated in FIGS. 4 and 5, the applique 50 has a generally rectangular, striplike configuration, although other configurations are also possible. For example, the applique may have a substantially straight upper edge to match the occlusal edges of the teeth 54, and a scalloped lower edge to match the shape of the gingival margin. In practice, however, satisfactory results have been obtained with the generally rectangular shape shown in FIGS. 4 and 5. Since the medication in the tray slowly escapes from the reservoir created by the applique 50 and contacts adjacent tooth structure while the tray is in use, substantially all of the buccolabial surfaces of the teeth underlying the applique 50 are subjected to the medication. For example, if the medication is a dental bleaching agent, the escape of the bleaching agent from the reservoir ensures that the entire buccolabial surface of each tooth is uniformly bleached to generally the same color, even though the reservoir does not extend over gingival portions of the buccolabial tooth surfaces.

Alternatively, medication delivery trays according to the invention may also be made using appliques of other shapes or sizes, using appliques made of other materials or using appliques in different methods for making the tray. Such alternative appliques and methods are described in applicant's pending U.S. patent application Ser. No. 09/217765 (attorney docket number 53911USA8B) entitled "MEDICATION DELIVERY TRAY", the disclosure of which is expressly incorporated by reference herein.

Moreover, any of the techniques described above for making a dental tray may include as an option the use of a dental model that is made using digital data instead of a dental model that is cast from a dental impression. For example, a model arch similar to the model 30 or 52 may be prepared by generating digital information defining the shape of the patient's dental arch, and then using the digital information to create the model. Optionally, the digital information may be created by the methods set out in PCT application no. WO 97/03622. In brief, PCT application no. WO 97/03622 describes a method of generating digital information of a patient's dental arches by making an impression of the patient's arches, and then removing a layer from the impression (or alternatively removing a layer from a model made from the impression) to obtain a flat surface; a video camera or other device is then used to collect digital data of the flat surface and the method is repeated; finally, the data is combined to provide a data set representative of the configuration of the patient's dental arches. Stereolithographic apparatus can then be used to make the model arch.

Other means for generating digital information of the patient's dental arch may also be employed. For example, the digital information may be generated electromechanically (e.g., by stylus scanning), by laser scanning, by photogammetry, by sonic ranging, by digital video scanning or magnetically. Examples of devices for generating the information are described in an article by Rekow entitled "Computer Aided Design and Manufacture in Dentistry: A Review of the State of the Art", from the *Journal of Prosthetic Dentistry*, Vol. 58, page 512 (1987). Other examples are described in U.S. Pat. Nos. 5,078,599, 5,131, 844, 5,338,198, 4,611,288 and 5,372,502 as well as in an article entitled "Three-dimensional dental cast analyzing system with laser scanning" (Kuroda, et al., *Am. J. Ortho. Dent. Othrop.*, Vol. 110 [4], October 1996, pages 365–69).

The medication delivery tray in accordance with the present invention is particularly suited for patients who desire to bleach their teeth. A common dental bleaching agent contains about 10% to about 16% carbamide peroxide, also called urea hydrogen peroxide, urea peroxide, hydrogen peroxide carbamide and perhydrol-urea. Carbamide peroxide has been used by dental clinicians since the 1960's as an oral antiseptic. Tooth whitening was a side effect of extended contact time. Over the counter ("OTC") compositions of 10% carbamide peroxide are available as "Gly-Oxide" by Marion Laboratories and "Proxigel" by Reed and Carnrick. A preferred dental bleaching agent comprises 64.86% propylene glycol, 21.00% glycerol, 1.5% carboxypolymethylene (e.g. Carbopol brand No. 980), 2.34% tris (hydroxymethyl)aminomethane, 0.30% mint flavor and 10.00% carbamide peroxide, with the viscosity increased by adjusting the pH to about 5.8.

A number of possible modifications and additions will become apparent to those skilled in the art after reviewing the description above. Accordingly, the invention should not be deemed limited to the specific, currently preferred embodiments that are described in detail above, but instead only by a fair scope of the claims that follow along with their equivalents.

What is claimed is:

1. A custom-made medication delivery tray for delivering medication to tooth structure of a dental patient comprising:

a body having a base, a buccolabial wall and a lingual wall, wherein the base, the buccolabial wall and the lingual wall present a channel generally complemental in configuration to the patient's tooth structure, wherein the buccolabial wall is adapted to extend at least in part along the gingival margin of the buccolabial side of the tooth structure without contacting the gingiva and wherein the lingual wall is adapted to extend along a line that is spaced at least in part at least 4 mm. in a gingival direction from the gingival margin of the tooth structure on a lingual side of the tooth structure.

2. A custom-made medication delivery tray according to claim 1 wherein the lingual wall extends along a line that is spaced at least in part at least 6 mm. in a gingival direction from the gingival margin from the tooth structure on a lingual side of the tooth structure.

3. A custom-made medication delivery tray according to claim 1 wherein the lingual wall extends along a line that is spaced no greater than 20 mm. in a gingival direction from the gingival margin of the tooth structure on a lingual side of the tooth structure.

4. A custom-made medication delivery tray according to claim 1 wherein the lingual wall extends along a line that is spaced no greater than 12 mm. in a gingival direction from the gingival margin of the tooth structure on a lingual side of the tooth structure.

5. A custom-made medication delivery tray according to claim 1 wherein the lingual wall includes an outer edge that extends along a line that decreases in spacing from the gingival margin of the tooth structure on a lingual side of the tooth structure as distal ends of the channel are approached.

6. A custom-made medication delivery tray according to claim 1 wherein the body is made from a sheet member having a thickness of about 1 mm or less.

7. A custom-made medication delivery tray according to claim 1 wherein the buccolabial wall includes at least one medication reservoir.

8. A method of making a medication delivery tray for delivering medication to dental structure of a patient comprising the acts of:

providing a model of at least a portion of a dental arch;

forming a sheet member over at least part of the model; and trimming the sheet member to make the tray, wherein the act of trimming the sheet member includes the act of trimming the sheet member along a path corresponding to a line spaced no greater than 1.0 mm in an occlusal direction from a the gingival margin of the model on a buccolabial side of the model and also includes the act of trimming the sheet member along a path corresponding to a line that is spaced at least in part at least 4 mm. in a gingival direction from the gingival margin of the model on a lingual side of the model.

9. A method of making a medication delivery tray according to claim 8 wherein the act of trimming the sheet member includes the act of trimming the sheet member along a line that is spaced at least in part at least 6 mm. in a gingival direction from the gingival margin of the model on a lingual side of the model.

10. A method of making a medication delivery tray according to claim 8 wherein the act of trimming the sheet member includes the act of trimming the sheet member along a line that is spaced no greater than 20 mm. in a gingival direction from the gingival margin of the model on a lingual side of the model.

11. A method of making a medication delivery tray according to claim 8 wherein the act of trimming the sheet member includes the act of trimming the sheet member along a line that is spaced no greater than 12 mm. in a gingival direction from the gingival margin of the model on a lingual side of the model.

12. A method of making a medication delivery tray according to claim 8 wherein the act of trimming the sheet member includes the act of trimming the sheet member along a line that is spaced a decreasing dimension in a gingival direction from the gingival margin of the model on a lingual side of the model as at least one distal end of the tray is approached.

13. A method of making a medication delivery tray according to claim 8 wherein the act of forming a sheet member over at least part of the model includes the act of providing a sheet member having a thickness of about 1 mm or less.

14. A method of making a medication delivery tray according to claim 8 wherein the act of forming a sheet member over at least part of the model includes the act of making at least one medication reservoir in a buccolabial wall of the tray.

15. A method of making a medication delivery tray according to claim 8 wherein the act of trimming the sheet member is carried out after the sheet member has been detached from the model.

16. A method of making a medication delivery tray according to claim 8 wherein the act of trimming the sheet member is carried out while the sheet member is connected to the model.

17. A method of making a medication delivering tray according to claim 8 wherein the act of trimming the sheet member includes the act of trimming the sheet member as necessary to provide a palatal region.

* * * * *